United States Patent
Wang

(10) Patent No.: US 8,295,921 B2
(45) Date of Patent: Oct. 23, 2012

(54) APPARATUS AND METHOD FOR NON-CONTACT ELECTRICAL IMPEDANCE IMAGING

(75) Inventor: Wei Wang, Leicester (GB)

(73) Assignee: De Montfort University, Leicester (GB)

( * ) Notice: Subject to any disclaimer, the term of this patent is extended or adjusted under 35 U.S.C. 154(b) by 595 days.

(21) Appl. No.: 11/990,093

(22) PCT Filed: Aug. 3, 2006

(86) PCT No.: PCT/GB2006/002887
§ 371 (c)(1),
(2), (4) Date: Jun. 2, 2010

(87) PCT Pub. No.: WO2007/017634
PCT Pub. Date: Feb. 15, 2007

(65) Prior Publication Data
US 2010/0241022 A1  Sep. 23, 2010

(30) Foreign Application Priority Data
Aug. 5, 2005  (GB) .................................. 0516158.3

(51) Int. Cl.
*A61B 5/05*  (2006.01)
(52) U.S. Cl. ...................................................... 600/547
(58) Field of Classification Search .................. 600/547
See application file for complete search history.

(56) References Cited

U.S. PATENT DOCUMENTS

| | | | | |
|---|---|---|---|---|
| 4,486,835 A | * | 12/1984 | Bai et al. ........................ | 378/21 |
| 4,920,490 A | * | 4/1990 | Isaacson ........................ | 600/547 |
| 4,986,275 A | * | 1/1991 | Ishida et al. .................. | 600/439 |
| 5,284,142 A | * | 2/1994 | Goble et al. .................. | 600/547 |
| 5,381,333 A | * | 1/1995 | Isaacson et al. ............... | 600/547 |
| 5,588,429 A | * | 12/1996 | Isaacson et al. ............... | 600/547 |
| 5,807,251 A | * | 9/1998 | Wang et al. ................... | 600/407 |
| 5,903,357 A | * | 5/1999 | Colak ........................... | 356/432 |
| 5,919,142 A | * | 7/1999 | Boone et al. .................. | 600/547 |
| 6,157,697 A | * | 12/2000 | Mertelmeier et al. ........... | 378/37 |
| 6,421,559 B1 | * | 7/2002 | Pearlman ...................... | 600/547 |
| 6,501,984 B1 | * | 12/2002 | Church et al. ................. | 600/547 |
| 6,535,796 B1 | * | 3/2003 | Sierro et al. .................. | 700/281 |
| 6,560,480 B1 | * | 5/2003 | Nachaliel et al. ............. | 600/547 |
| 6,622,035 B1 | * | 9/2003 | Merilainen et al. ............ | 600/391 |

(Continued)

FOREIGN PATENT DOCUMENTS

JP  5056940  3/1993

(Continued)

OTHER PUBLICATIONS

Y. Zou, et al.; "A review of electrical impedance techniques for breast cancer detection;" Medical Engineering & Physics, vol. 25; Mar. 2003; pp. 79-90, p. 82 Table 1, p. 84 section 3.1.2.

(Continued)

*Primary Examiner* — Max Hindenburg
*Assistant Examiner* — Michael C Stout
(74) *Attorney, Agent, or Firm* — Ware, Fressola, Van Der Sluys & Adolphson LLP

(57) ABSTRACT

A method of electrical impedance imaging using multiple electrodes in which each of the multiple electrodes does not contact the object to be imaged but is electrically coupled to the object via electrically conductive fluid in which the object is at least partially immersed.

30 Claims, 1 Drawing Sheet

U.S. PATENT DOCUMENTS

| | | | |
|---|---|---|---|
| 6,678,552 B2* | 1/2004 | Pearlman | 600/547 |
| 6,922,586 B2* | 7/2005 | Davies | 600/547 |
| 7,007,867 B1* | 3/2006 | Drapeau | 239/394 |
| 7,499,745 B2* | 3/2009 | Littrup et al. | 600/547 |
| 7,627,362 B2* | 12/2009 | Gregory et al. | 600/427 |
| 8,010,187 B2* | 8/2011 | Freed et al. | 600/547 |
| 2001/0051774 A1* | 12/2001 | Littrup et al. | 600/547 |
| 2002/0106681 A1* | 8/2002 | Wexler et al. | 435/6 |
| 2002/0138019 A1* | 9/2002 | Wexler et al. | 600/547 |
| 2003/0192784 A1* | 10/2003 | Zhou | 205/109 |
| 2004/0064046 A1* | 4/2004 | Shehada | 600/437 |
| 2004/0078915 A1* | 4/2004 | Hockey-Smith et al. | 15/228 |
| 2004/0167421 A1* | 8/2004 | Gregory et al. | 600/547 |
| 2004/0253652 A1* | 12/2004 | Davies | 435/7.23 |
| 2005/0203436 A1* | 9/2005 | Davies | 600/547 |
| 2006/0063062 A1* | 3/2006 | Zhou et al. | 429/40 |
| 2006/0241514 A1* | 10/2006 | Davies | 600/547 |
| 2007/0089994 A1* | 4/2007 | Zhou | 205/264 |
| 2008/0004543 A1* | 1/2008 | Davies | 600/547 |
| 2008/0200793 A1* | 8/2008 | Furue et al. | 600/393 |
| 2008/0300472 A1* | 12/2008 | Van Der Mark et al. | 600/323 |
| 2010/0241022 A1* | 9/2010 | Wang | 600/547 |

FOREIGN PATENT DOCUMENTS

| | | |
|---|---|---|
| JP | 7031598 | 2/1995 |
| WO | WO 00/12005 | 3/2000 |
| WO | WO 2004/043253 | 5/2004 |

OTHER PUBLICATIONS

A. Malich, et al; "Electrical impedance scanning for classifying suspicious breast lesions: first results;" European Radiology, vol. 10, No. 10; Sep. 2000; pp. 1555-1561, whole document.

A. Malich, et al; "Electrical impedance scanning as a new imaging modality in breast cancer detection—a short review of clinical value on breast application, limitations and perspectives;" Nuclear Instruments & Methods in Physics Research, Section A: Accelerators, Spectrometers, Detectors and Associated Equipment; Elsevier, Amsterdam, NL; vol. 497, No. 1; Jan. 21, 2003; pp. 75-81, whole document.

* cited by examiner

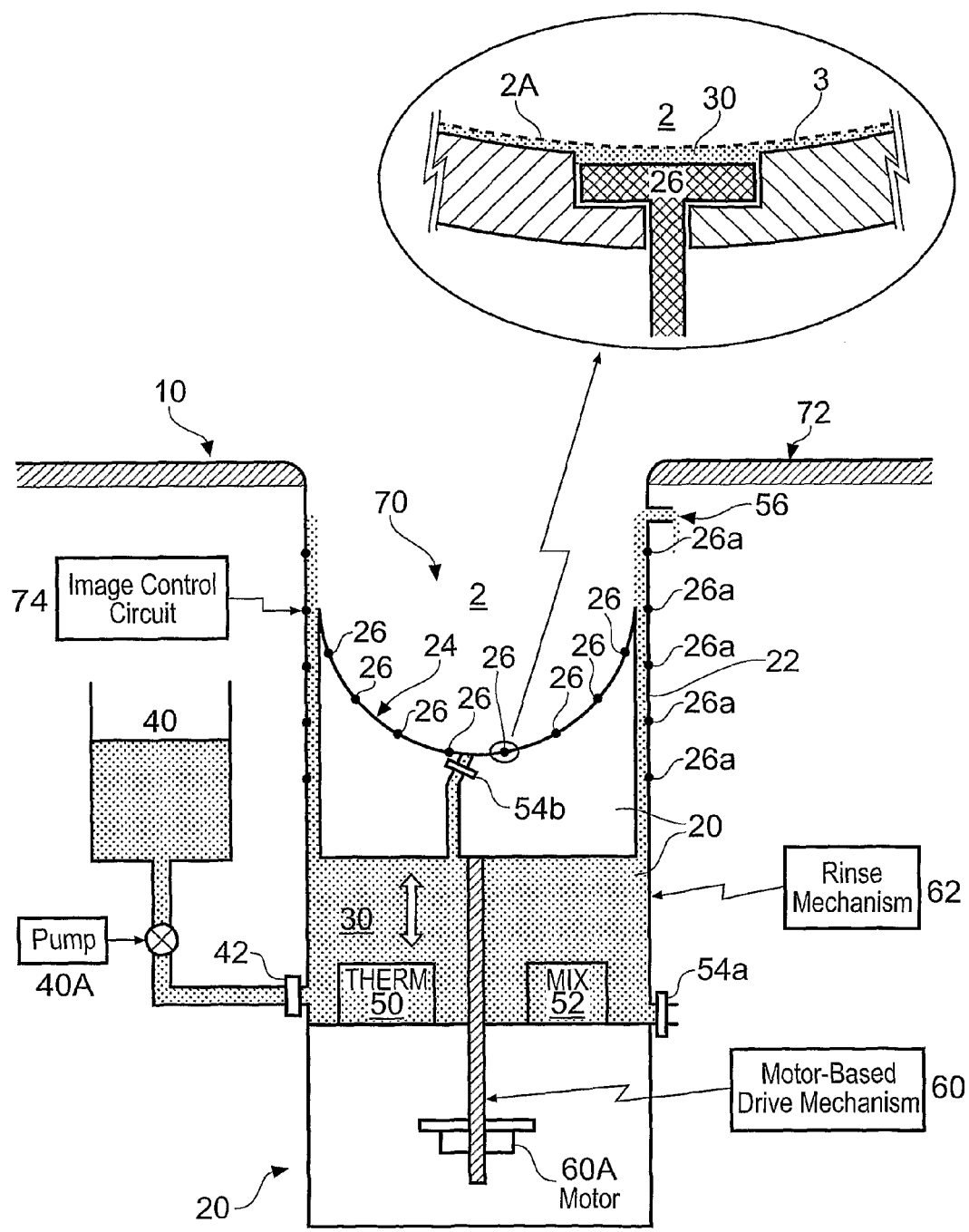

APPARATUS AND METHOD FOR NON-CONTACT ELECTRICAL IMPEDANCE IMAGING

CROSS REFERENCE TO RELATED APPLICATIONS

This application is the U.S. National Stage of International Application Number PCT/GB2006/002887 filed on Aug. 3, 2006 which was published in English on Feb. 15, 2007 under International Publication Number WO 2007/017634.

FIELD OF THE INVENTION

Embodiments of the present invention relate to an apparatus and method for electrical impedance imaging.

BACKGROUND TO THE INVENTION

Electrical impedance mammography (EIM), or Electrical impedance imaging (EII), also referred to as electrical impedance tomography (EIT), electrical impedance scanner (EIS) and applied potential tomography (APT), is an imaging technique that is particularly used in medical applications.

The technique images the spatial distribution of electrical impedance inside an object, such as the human body. The technique is attractive as a medical diagnostic tool because it is non-invasive and does not use ionizing radiation as in X-ray tomography or the generation of strong, highly uniform magnetic fields as in Magnetic Resonance Imaging (MRI).

Typically a two-dimensional (2D) or three-dimensional (3D) array of evenly spaced electrodes is attached to the object to be imaged about the region of interest. Either input voltages are applied across pairs of 'input' electrodes and output electric currents are measures at the 'output' electrodes or input electric currents are applied between pairs of 'input' electrodes and output voltages are measured between at the 'output' electrodes or between pairs of output electrodes. For example, when a very small alternating electric current is applied between a pair of 'input' electrodes, the potential difference between all other pairs of 'output' electrodes is measured. The current is then applied between a different pair of 'input' electrodes and the potential difference between all other pairs of 'output' electrodes is measured. An image is constructed using an appropriate image reconstruction technique.

Spatial variations revealed in electrical impedance images may result from variations in impedance between healthy and non-healthy tissues, variations in impedance between different tissues and organs or variations in apparent impedance due to anisotropic effects resulting for example from muscle alignment.

Tissue or cellular changes associated with cancer cause significant localized variations in electrical impedance and can be imaged. WO 00/12005 discloses an example of electrical impedance imaging apparatus that can be used to detect breast carcinomas or other carcinomas.

A most common problem associated with impedance imaging is that there are unexpected and unknown electrical impedances present other than those provided by the object to be imaged. The unexpected and unknown electrical impedances may arise from the imaging electrode sensor system and the associated changes in electrical impedance may be much greater than the internal electrical impedance of the object and its changes and may therefore mask local variations in the internal electrical impedance of the object or changes in such impedances. For example, the imperfect contact between an electrode and the object to be imaged introduces an impedance at each electrode. Such an impedance may vary in an unknown manner from electrode to electrode or vary over time or varying depending on how the electrode has been attached to the object. This can introduce significant unpredictable errors into the produced image and can therefore result in an unrepeatable image being produced. This will prevent the accurate detection and monitoring of the development of, for example, non-healthy tissue.

BRIEF DESCRIPTION OF THE INVENTION

According to one embodiment of the invention there is provided a method of electrical impedance imaging using multiple electrodes in which each of the multiple electrodes does not contact the object to be imaged but is electrically coupled to the object via special conducting fluid in which the object is at least partially immersed.

One advantage of having a continuum of fluid intervene between each electrode and the object instead of having the electrodes directly contact the object is that not only does it substantially standardise the impedance between each electrode and the object, but it also achieves "perfect" contact between electrode and object based on "sizeless" ions. This allows for more reliable imaging.

The fluid is typically electrically conductive. It may be a liquid (or a gel) that comprises ions. The conductivity of the fluid may be carefully controlled by controlling the concentration of ions. The ions may include Group I metal ions such as Na+. The ions may include Group VII halide ions such as Cl−.

An advantage of using a fluid comprising ions is that the conductive mechanism between the electrode and the object is 'electrode-ions-object' based on "sizeless" ions. This conduction mechanism provides a "perfect" contact between the electrode and the object with known "half-cell" potentials once the electrode material is chosen. As the conduction mechanism is not a typical "electrode-skin interface" it does not suffer the disadvantages associated with any "contact" based "electrode-skin interface" namely an unknown effective contact area which provides an unknown contact impedance including associated capacitance from the "electrode-skin interface". The electrode-ion-object conduction mechanism is not dependent upon the contact area between the electrode and the object. This allows the use of smaller electrodes, which allows a greater number of electrodes to be used to image an object, which in turn provides greater resolution in the image produced.

The temperature of the fluid is thermostatically controlled at a fixed temperature close to human body temperatures. An advantage of maintaining the temperature at a constant value is that the impedance between each electrode and the object remains constant over time. This prevents variation in the impedance of the fluid introducing errors.

A housing of variable volume receives the object and the volume of the housing is varied to correspond to the size of the object. This allows the method to be used with objects of different size. It also provides for highly repeatable measurements for any dedicated size of the object. The array of electrodes typically changes with a change in volume of the housing, with more electrodes being used for objects of larger size. The size of the object therefore determines the volume of the housing which determines the arrangement of electrodes.

The algorithm used to image an object may take as an input an indication of the volume of the housing. The volume is associated with a particular known arrangement of electrodes, and knowledge of this arrangement can be used in the algorithm to improve the accuracy of the image produced. To be able to reconstruct a high-quality image by a selected imaging reconstruction algorithm, it is required to know the exact correct positions of each electrode and its relation to the object to be imaged so that the errors between the ideal electrode positions used by the algorithms and actual positions of the electrodes will be significantly minimized. Furthermore, to be able to reconstruct a highly repeatable image for diagnosis, it is necessary for the object to be in a similar geometry and three dimensional position for each measurement so that the image collected from a different time and even from a different hospital with the same model of EIM device can be highly comparable. To achieve this, the same volume and therefore the same electrode arrangement may be used in a series of distinct and separate imaging procedures for the same patient, so that the images produced in each procedure are comparable. This improves the repeatability of an imaging procedure and allows the development of unhealthy tissue in a breast, for example, to be accurately detected and monitored over time. In particular, it allows a technician or operator to be able to distinguish two separate areas of healthy and unhealthy tissues and monitor their development.

According to another embodiment of the invention there is provided an apparatus for electrical impedance imaging comprising: a housing having a cavity for containing a fluid in which an object to be imaged is at least partially immersed; and a plurality of electrodes positioned at the periphery of the cavity, wherein in use each of the plurality of electrodes does not contact the object to be imaged but is electrically coupled to the object via the fluid in which the object is immersed.

BRIEF DESCRIPTION OF THE DRAWINGS

For a better understanding of the present invention reference will now be made by way of example only to the accompanying drawings in which:

FIG. 1 illustrates an apparatus 10 for electrical impedance imaging of an object 2.

DETAILED DESCRIPTION OF EMBODIMENT(S) OF THE INVENTION

FIG. 1 illustrates an apparatus 10 for electrical impedance imaging of an object 2. The apparatus 10 comprises: a housing 20 having a cavity 70 for containing a fluid 30 in which an object 2 to be imaged is at least partially immersed; and a plurality of electrodes 26, 26A positioned at the periphery of the cavity 70. In use, each of the electrodes 26, 26A does not contact the object 2 to be imaged but is electrically coupled to the object 2 via the fluid 30 in which the object 2 is immersed.

The apparatus 10 described in the following paragraphs has been adapted for use in electrical impedance imaging of a human breast, particularly the female breast.

The female lies on a table 72 and places her breast into a cavity 70 that is already filled with fluid 30 or is subsequently filled with fluid 30. The cavity 70 has a variable volume and is sized to match the size of the breast 2 to be imaged.

The cavity 70 is defined by a housing 20 which comprises a cylindrical tubular wall portion 22 of fixed size and a movable cup portion 24. The cup portion 24 is typically a section of an ellipsoid or a hemisphere.

A drive mechanism 60 is used to move the cup portion 24 up or down and thereby vary the volume of the housing cavity 70 so that it corresponds to the size of the breast 2. The drive mechanism 60 includes a feedback circuit for automatically adjusting the volume of the housing cavity so that it correctly corresponds to the size of a received breast 2. While the breast 2 is received within the cavity 70, the drive mechanism 60 raises the cup portion until the breast 2 slightly resists further upward movement, the mechanism in response to this feedback then lowers the cup portion 24 slightly by a standard amount to create a small gap 3 between the cup portion and the breast skin 2A that is filled by fluid 30.

In other embodiments, the diameter of the cylindrical tubular wall may also or alternatively be varied. A feedback mechanism may also be used to ensure that the width as well as the depth of the cavity correctly corresponds to the size of the received breast.

Each electrode 26 is fixed in a known position and is recessed from the surface of the cup portion 24 and each electrode 26A is fixed in a known position and recessed from the surface of the cylinder 22. This recessing helps prevent the breast skin 2A from contacting electrodes 26, 26A.

The electrodes 26 are arranged as a spaced regular array over the surface of the cup portion 24. Electrodes 26A are arranged as a spaced regular array over the surface of the cylinder 22. As the cup portion 24 is lowered, more of the electrodes 26A are included within the cavity 70 and as the cup portion 24 is raised, less of the electrodes 26A are included within the cavity. The distance between each one of the electrodes 26, 26A and the breast skin 2A via the fluid 30 is significantly less that the distance between adjacent electrodes 26 or 26A via the fluid and is typically less than 5 mm.

The size and roughness of all the electrodes surface (interface to conducting fluid) is preferably the same.

Imaging control circuitry 74 is connected to the electrodes 26. It comprises electrical signal generating circuitry for passing an input electric current via a first set of two electrodes 26 while measuring the output potential differences at a second set of electrodes 26. The electric current typically comprises a plurality of different frequencies and at least some frequencies above 1 MHz. Frequencies from 100 Hz to above 1 MHz (preferably 10 MHz) have been used with the frequency bandwidth exceeding 1 MHz. In other embodiments, the electrical signal generating circuitry provides an input potential difference across a first set of two electrodes while measuring output electric currents at a second set of electrodes 26. The applied potential difference typically comprises a plurality of different frequencies and at least some frequencies above 1 MHz.

The total impedance of a tissue or group of cells can be modelled as a parallel intra-cellular impedance and a parallel extra-cellular impedance. The intra-cellular impedance can be modelled as a series connection of a capacitance $C_i$ and a resistance $R_i$. The extra-cellular impedance can be modelled as a resistance $R_x$. At lower frequencies the total impedance is dominated by $R_x$ and at higher frequencies the total impedance is dominated $R_i//R_x$. The frequency response is sensitive to variations in $C_i$, $R_i$ and $R_x$ and can be used to identify the presence of abnormal tissue.

The image control circuitry 74 successively changes the first and second set of electrodes 26 to collect output data for imaging the breast 2. The measured outputs are converted from analogue to digital and processed using, for example, commercially available software to produce a 2D or 3D image of the breast 2. An abnormality of tissue such as a carcinoma will typically appear as a contrast region in the image.

The fluid 30 is an electrically conductive fluid that comprises ions. A suitable fluid is an aqueous saline solution but other electrolytes may be used. The concentration of the saline solution can be controlled so that the conductivity of the fluid is less than or equal to that of the breast 2 or alternatively so that it has an electrical impedance matched to that of the breast 2. For hygiene reasons, the fluid 30 may contain anti-bacterial and/or anti-fungicidal agents.

The fluid 30 is provided to the housing cavity 70 from a reservoir 40 via a one-way inlet valve 42. The fluid 30 is released, after measurement, from the cavity via an internal valve 54B and an outlet valve 54. Overflow of fluid displaced by the breast 2 onto the table 72 is prevented by overflow outlet 56.

The housing cavity 70 also comprises a thermostatic control system 50 for maintaining the temperature of the fluid 30 in the housing cavity 70 at a constant value.

A mixer 52 is also located within the housing cavity 70. It is used for moving the fluid 30 in the cavity to maintain homogeneity of temperature within the fluid 30 and homogeneity of concentration of the fluid 30.

A rinse mechanism 62 is used to rinse the emptied housing cavity 70 with an anti-bacterial and/or anti-fungicidal agent between use of the apparatus by different subjects.

Although embodiments of the present invention have been described in the preceding paragraphs with reference to various examples, it should be appreciated that modifications to the examples given can be made without departing from the scope of the invention as claimed. For example, although the method and apparatus have been described for imaging a breast they may be simply adapted to image the cardiac muscle.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of electrical impedance imaging comprising: using multiple recessed electrodes in which each of the multiple recessed electrodes does not contact an object to be imaged but is electrically coupled to the object via an electrically conductive fluid in which the object is at least partially immersed;
   using a housing for the recessed electrodes to contain the fluid and varying dimensions of the housing to correspond to the size of the object:
   wherein a first housing portion has a first plurality of recessed electrodes and a second housing portion has a second plurality of recessed electrodes and
   wherein relative movement of the first housing portion and the second housing portion varies a proportion of the second plurality of recessed electrodes that are exposed for electrical coupling to the object via the electrically conductive fluid in which the object is at least partially immersed.

2. The method as claimed in claim 1, wherein the electrically conductive fluid comprises ions.

3. The method as claimed in claim 1, wherein the electrically conductive fluid has an electrical conductivity equal or less than that of the object.

4. The method as claimed in claim 1, wherein the electrically conductive fluid has an electrical impedance matched to that of the object.

5. The method as claimed in claim 1, wherein the electrically conductive fluid is an aqueous saline solution of controlled molarity.

6. The method as claimed in claim 1, wherein the fluid comprises anti-bacterial and/or anti-fungicidal agents.

7. The method as claimed in claim 1, wherein the temperature of the fluid is thermostatically controlled.

8. The method as claimed in claim 1, wherein relative movement of the first housing portion and second housing portion changes the number and/or configuration of the multiple recessed electrodes.

9. The method as claimed in claim 1, wherein the object is a human breast and the second housing portion comprises a cup movable within the first housing portion which comprises a receptacle.

10. The method as claimed in claim 1, further comprising applying an input electrical signal via a pair of the multiple recessed electrodes while simultaneously measuring output electrical signals using other ones of the multiple recessed electrodes.

11. The method as claimed in claim 10, wherein the input electrical signal is applied at a plurality of frequencies having a bandwidth greater than 1 MHz.

12. An apparatus for electrical impedance imaging comprising:
    a housing having a cavity for containing a fluid in which an object to be imaged is capable of being at least partially immersed;
    a plurality of recessed electrodes positioned at the periphery of the cavity, wherein the apparatus is configured such that in use each of the plurality of recessed electrodes does not contact the object to be imaged but is electrically coupled to the object via the fluid in which the object is immersed; and
    a drive mechanism configured to move a first housing portion relative to a second housing portion to vary a volume of the housing cavity to correspond to the size of the object.

13. The apparatus as claimed in claim 12, further comprising a drive mechanism configured to move a first housing portion relative to a second housing portion to vary a volume of the housing cavity to correspond to the size of the object.

14. The apparatus as claimed in claim 13, wherein the apparatus comprises a multiplicity of recessed electrodes and varying the volume of the housing changes which of the multiplicity of recessed electrodes are exposed to operate as said plurality of recessed electrodes.

15. The apparatus as claimed in claim 13, wherein the recessed electrodes are arranged in a first array at the first housing portion and a second array at the second housing portion, wherein the first housing portion movable relative to the second housing portion to vary dimensions of the cavity.

16. The apparatus as claimed in claim 15, wherein the first housing portion has a first plurality of recessed electrodes and the second housing portion has a second plurality of recessed electrodes and wherein movement of the first housing portion varies an extent to which the second plurality of recessed electrodes are exposed.

17. The apparatus as claimed in claim 13, further comprising a feedback circuit for the drive mechanism for adjusting the volume of the housing cavity so that the cavity corresponds to the size of the object.

18. The apparatus as claimed in claim 15, wherein the object is a human breast, the first housing portion is a cup and the second housing portion is a receptacle.

19. The apparatus as claimed in claim 12, wherein, the apparatus is configured such that in use, the distance between each one of the recessed electrodes and the object via the fluid is less that rhea distance between adjacent recessed electrodes via the fluid.

20. The apparatus as claimed in claim 19, wherein, the apparatus is configured such that in use, the distance between each one of the recessed electrodes and the object via the fluid is less than 5 mm.

21. The apparatus as claimed in claim 12, further comprising circuitry configured to apply an input electrical signal using a first set of the plurality of recessed electrodes while measuring output electrical signals at a second different set of the plurality of recessed electrodes.

22. The apparatus as claimed in claim 12, further comprising a fluid reservoir, an inlet from the reservoir to the housing cavity for providing fluid, a drain for draining fluid from the housing cavity and an overflow for channelling fluid that overflows from the housing cavity.

23. The apparatus as claimed in claim 12, further comprising a mechanism configured to rinse the housing cavity with an anti-bacterial and/or anti-fungicidal agent.

24. The apparatus as claimed in claim 12, further comprising a thermostatically controlled system for maintaining the temperature of the fluid in the housing cavity.

25. The apparatus as claimed in claim 12, further comprising a mixer configured to move the fluid in the cavity to maintain homogeneity.

26. A method of electrical impedance imaging using multiple electrodes comprising:

at least partially immersing an object to be imaged in an electrically conductive fluid contained in a housing for multiple electrodes, wherein each of the multiple electrodes does not contact the object but is electrically coupled to the object via the electrically conductive fluid, wherein the multiple electrodes are arranged in a first array at a surface of a cup and a second array at a surface of a receptacle and wherein the cup is movable relative to the receptacle to vary dimensions of the housing.

27. The apparatus as claimed in claim 26, wherein the receptacle is cylindrical in shape.

28. The method as claimed in claim 1, wherein the second housing portion comprises a surface defining a cavity and wherein the multiple recessed electrodes are recessed from the surface.

29. The method as claimed in claim 28, further comprising varying a volume of the housing, by the relative movement of the first and second portions, by bringing the surface defining the cavity into contact with the object.

30. The method as claimed in claim 29, further comprising decreasing the volume of the housing until the object resists decreasing the volume of the housing, and then increasing the volume of the housing.

* * * * *